United States Patent
Starkey

(12) United States Patent (10) Patent No.: US 7,530,998 B1
Starkey (45) Date of Patent: May 12, 2009

(54) DEVICE AND METHOD TO CONTROL VOLUME OF A VENTRICLE

(76) Inventor: Thomas David Starkey, 420 ½ Lynwood Dr., Nashville, TN (US) 37205

( * ) Notice: Subject to any disclaimer, the term of this patent is extended or adjusted under 35 U.S.C. 154(b) by 411 days.

(21) Appl. No.: 11/350,480

(22) Filed: Feb. 9, 2006

Related U.S. Application Data

(62) Division of application No. 10/619,985, filed on Jul. 15, 2003, now Pat. No. 7,341,584.

(60) Provisional application No. 60/474,310, filed on May 30, 2003.

(51) Int. Cl.
*A61M 1/10* (2006.01)
*A61N 1/362* (2006.01)

(52) U.S. Cl. .............. 623/3.1; 600/16; 600/37
(58) Field of Classification Search ........... 623/3.1, 623/3.16, 3.17, 3.21; 60/16, 17, 37
See application file for complete search history.

(56) References Cited

U.S. PATENT DOCUMENTS 5,139,517 A * 8/1992 Corral .................. 623/3.1

* cited by examiner

*Primary Examiner*—Bruce E Snow
(74) *Attorney, Agent, or Firm*—Waddey & Patterson, PC; I. C. Waddey, Jr.

(57) ABSTRACT

A device used to treat heart disease by decreasing the size of a diseased heart, or to prevent further enlargement of a diseased heart. The device works by limiting the volume of blood entering the heart during each cardiac cycle. The device partitions blood within the heart, and protects the heart from excessive volume and pressure of blood. The device is placed within the interior of the heart, particularly within a ventricular cavity. The device is a hollow sac, with two openings, which simulates the shape and size of the interior lining of a ventricle of a normal heart. It allows the ventricle to fill through one opening juxtaposed to the annulus of the inflow valve to a predetermined, normal volume, and limits filling of the heart beyond that volume. It then allows blood to be easily ejected through the second opening through the outflow valve. By limiting the amount of blood entering the ventricle, the ventricle is not subjected to the harmful effect of excessive volume and pressure of blood during diastole, the period of the cardiac cycle when the heart is at rest. This allows the heart to decrease in size, or to reverse remodel, and to recover lost function. In some applications, a second device may be simultaneously placed inside the heart to take up excessive space between the heart and the primary device.

14 Claims, 6 Drawing Sheets normal heart heart failure heart failure with divola / VCD excessive volume of VCD

DEVICE AND METHOD TO CONTROL VOLUME OF A VENTRICLE

CROSS-REFERENCES TO RELATED APPLICATIONS

This application is a Divisional application which claims benefit of U.S. patent application Ser. No. 10/619,985 filed Jul. 15, 2003 now U.S. Pat. No. 7,341,584, entitled "A Device and Method to Limit Filling of the Heart" which is hereby incorporated by reference and which claims benefit of U.S. Patent Application Ser. No. 60/474,310 filed May 30, 2003, entitled "Heart Liner to Limit Volume of Blood Accepted in the Heart to Allow Heart to Regenerate Itself to a Normal Size" which is hereby incorporated by reference.

STATEMENT REGARDING FEDERALLY SPONSORED RESEARCH OR DEVELOPMENT

The research and development leading to the present invention was not federally sponsored.

BACKGROUND OF THE INVENTION

The invention described in this application pertains to the class of medical devices used to treat heart disease that function to decrease the size of the heart, or to prevent enlargement of the heart.

Heart disease is common in our society, and the incidence is rapidly increasing. One class of heart disease, heart failure, affects 4 to 5 million patients in the United States, with up to two million hospitalizations per year. This accounts for 2 to 3 percent of the national healthcare budget. The American Heart Association reports a continue increase in the incidence of heart failure in the United States, with 51,546 deaths reported in 2000. There were 999,000 hospital discharges with diagnosis of congestive heart failure (ICD/9 428.0, ICD10/150.0) in year 2000, at an estimated healthcare cost of US$24.3 billion. There were 27,213 deaths from cardiomyopathy (ICD/9 425, ICD/10 142), (87% either congestive or dilated) in 2000, with total mentioned mortality of 54,900, and 31,000 hospital discharges.

Causes of cardiomyopathy and congestive heart failure include hypertension, valvular heart disease, and ischemic heart disease, manifest by left ventricular aneurysms or global enlargement of the left ventricle. Other causes of heart failure include some forms of congenital heart disease, viral cardiomyopathy, where the heart enlarges secondary to a viral infection, and idiopathic dilated cardiomyopathy, where the heart enlarges for unknown reasons.

In the early stages of heart disease the body conserves sodium by limiting excretion in the kidney. This increases the volume of blood presented to the heart. As described by the Frank-Starling mechanism, the heart works more efficiently with mild dilatation. However, this mechanism becomes ineffective, and actually deleterious, beyond a mild degree of dilatation. Excessive volume of blood and increased filling pressures may actually cause progressive dilatation of the heart. A vicious cycle of increased blood volume resulting in increased heart failure resulting in increased blood volume, etc., is started. The heart is particularly susceptible to dilatation from excessive pressure and volume during diastole, the period of the cardiac cycle when the heart is at rest.

The medical treatment of heart disease includes restriction of the oral intake of sodium, diuretic medications, direct vasodilators, and inhibitors of angiotensin converting enzyme. These modes of therapy are directed at decreasing the volume of blood in the circulatory system and the dimensions of the heart. As derived from physiological Law of LaPlace, the larger the heart is, the greater wall tension is required to generate a certain pressure within the heart. Remodeling, a term used to describe abnormal enlargement of the heart, causes the heart to function less efficiently. Greater energy or work is needed to generate satisfactory blood pressure and blood flow.

Although the medical treatment for heart disease and heart failure has progressed over the last decade, many patients require surgical therapy. Conventional surgical therapy includes coronary artery revascularization, valve repair or replacement, and treatment of ventricular aneurysms. Although many patients benefit significantly from surgery, some patients have progressive or continued cardiac enlargement. None of the modes of conventional cardiac surgery directly prevent progressive or persistent dilatation of the heart.

A recent report Bolling and others describes a high-risk group of patients with severely dilated hearts who undergo repair or replacement of the regurgitant mitral valve. This report demonstrates the feasibility of performing successful operations on such very sick patients. This report also demonstrates that the heart may shrink in size when excessive volume of blood in the heart is treated. Unfortunately, not all of the patients in this group had significant of long-term benefit, and some required transplantation. The use of the device(s) described in this patent application should prevent persistent and/or recurrent dilatation of the left ventricle in patients such as these.

An uncommon yet fatal complication of myocardial infarction is rupture of the left ventricle. The left ventricle can rupture in the free wall causing a cardiac tamponade, or it may rupture into the right ventricle, causing an ischemic ventricular septal defect. Currently there is no medical device that can be used to treat this fatal disease. The device described in this patent application could be used to treat this condition and effectively seal the rupture of the left ventricle.

An operation to remove a portion of the left ventricular wall was popularized in the mid 1990s by Randas Batista. This operation made the left ventricular chamber smaller, which allowed for improved hemodynamic function. Many patients underwent this surgical procedure, but most had recurrent dilated heart disease. The use of the invention described in this application in such a group of patients either as an alternative to this operation or in conjunction with this operation might prove beneficial.

A group of patents (U.S. Pat. Nos. 6,439,237; 6,221,104; 6,024,096) were recently issued pertaining to a specialized technique of repair of ventricular aneurysms. After removal of excessive scar tissue from the aneurysm, a specialized patch is used to repair the aneurysm. This technique surgically decreases the size of the left ventricle, but unfortunately does not prevent progressive and recurrent dilatation of the heart. The device(s) described in this patent application might be used to augment the conventional repair of a ventricular aneurysm, preventing progressive or recurrent dilatation of the heart.

The concept of wrapping the heart with skeletal muscle, or dynamic cardiomyoplasty, was popularized in the last two decades. Only minimal improvement of the cardiac output is seen with this operation in both animals and humans. The benefit, if any, of this procedure likely comes from constraining or squeezing the heart to a smaller size. This operation does not directly limit the filling of the heart with blood. The device(s) described in this patent application might be used instead of dynamic cardiomyoplasty to treat these patients with heart disease.

One satisfactory means of treatment of extreme cases of heart disease is heart transplantation. There are unfortunately a limited number of donors, and only a very small fraction of patients who would benefit from heart transplantation are able to receive a donor heart. Heart transplantation requires immunosuppression, which has many serious and sometimes fatal side effects. Heart transplantation is extremely expensive, with the initial cost of approximately US$150,000 to 200,000, and recurrent yearly costs of approximately US$25,000 to 40,000. The average lifespan of a patient after heart transplant is 8 years.

An ever-expanding mode of therapy for advance heart disease is the use of a mechanical pumping device. These pumps were first used in the 1960s, and literally dozens of different types of pumps are currently in use or in various stages of development. These pumps are used either to assist the diseased heart or to completely replace the heart. Currently, the use of mechanical cardiac assist devices is limited by frequent and common complications of the implantation and use of the devices. The complications include thrombosis, thrombotic emboli causing stroke, organ, and limb ischemia, infection, particularly from the driveline, as well as catastrophic mechanical failure of the device. Furthermore, these devices are extremely expensive, with some costing approximately US$85,000.

Jarvik has described a novel use of mechanical pumping devices (U.S. Pat. No. 5,092,879) by placing the pump within the confines of the left ventricle. One embodiment of his invention is a muscle powered blood pump placed within the left ventricle of the heart. This device utilizes skeletal muscle excited by a pacemaker, wrapped around a complex sac. Unlike Jarvik's invention, the blood sac of the present invention very simple in design and construction. The sac is activated by the native heart, and does not require autotransplantation or homotransplantations of muscle tissue into the heart. The current invention allows for improvement of a diseased heart by limiting filling of the heart during diastole.

An intraventricular rotary blood pump is now in clinical use (Jarvik, U.S. Pat. No. 5,824,070), but with only modest improvement of the patients, and an important rate of complications. These intraventricular blood pumps do not directly or precisely limit filling of the left ventricular chamber of the heart.

A new class of medical devices has been developed to physically alter the shape and size of the heart. One group of such devices (U.S. Pat. Nos. 5,957,977; 6,190,408; 6,221,103; 6,409,760; 6,520,904) fit around and within the interior of the left ventricle to constrain the heart to a more normal size and shape. The multiple internal and external rigid members of this complex device press directly on the tissue of the heart. These devices may erode into the vital structure of the heart, possibly even perforating the heart. This device does not directly limit the volume of blood entering the left ventricle. Only modest improvement of cardiac function has been shown in a recent animal study reported by Kashem and others.

Another similar group of devices are placed on the surface to the heart (U.S. Pat. Nos. 6,332,864; 6,264,602; 6,183,411; 6,402,680; and 6,402,67X). These devices attempt to reshape and reduce the size of the heart. The rigid parts of these devices have the potential to erode into the vital structure of the heart, possibly even perforating the heart. These devices do not directly limit the volume of blood entering the left ventricle.

Yet another group of devices (U.S. Pat. Nos. 6,537,198; 6,514,194; 6,406,420; 6,332,893; 6,332,863; 6,261,222; 6,260,552; 6,165,120; 6,165,119; 6,162,168; 6,077,214; 6,059,715; 6,050,936; 6,045,0497; and 5,961,440) attempt to reshape the heart with a wire or wires traversing the left ventricular chamber of the heart. These devices have the potential to disrupt the mitral valve and subvalvular apparatus, as well as the potential to erode into other vital structure of the heart, possibly even perforating the heart. There is a potential for bleeding from the wires puncturing the left ventricular chamber of the heart. These devices do not directly limit the volume of blood entering the left ventricle of the heart. These devices do not prevent further dilatation of the heart, nor do they direct shrinking or reverse remodeling of the heart. Only modest improvement of cardiac function has been demonstrated in recent studies, as reported by Schenk and others.

Another series of devices described by Clifton Alferness (U.S. Pat. Nos. 6,537,203; 6,482,146; 6,375,608; 6,370,429; 6,241,654; 6,230,714; 6,169,922; 6,165,122; 6,165,121; 6,126,590; 6,123,662; 6,085,754; 6,077,218; and 5,702,343), Kay Nauertz and others (U.S. Pat. No. 6,155,972), Michael Girard (U.S. Pat. No. 6,174,279), Kurt Krueger (U.S. Pat. No. 6,193,648), Edward Shapland and others (U.S. Pat. No. 6,425,856), and Hans Handle (U.S. Pat. No. 6,416,459) consist of a bag which wraps around the heart to constrain the heart to a more favorable size and shape. The device has the potential to slip out of position, to constrict the heart, and to cause formation of scar tissue around the heart. This series of devices does not directly or precisely limit filling of the left heart with blood. Early reports on this series of devices have shown only marginal benefit.

It has been reported by Burkoff and other groups that the left ventricle of the heart will return to normal size when circulation is supported with a left ventricular assist device. A left ventricular assist device is a mechanical pump that augments the pumping action of the heart. Many patients who have had previous placement of a ventricular assist device benefit by shrinking of their enlarged heart to a more normal size and shape. This process of decreasing the size of an abnormally enlarged heart is referred to as "reverse remodeling". This effect of reverse remodeling demonstrates that if the left ventricle is no longer exposed to excessive pressure and volume of blood, it naturally shrinks to a more normal size and shape.

Some patients who have had significant reverse remodeling after placement of a left ventricular assist device chose to have the device removed. Of these patients who had removal of a device, some have had sustained benefit of the reverse remodeling, although many unfortunately have recurrent progression of their dilated heart disease. The invention described in this application could be used in such a group of patients to treat the heart disease, either used instead of a left ventricular assist device, or placed at the time of removal of the left ventricular assist device to prevent recurrent cardiac enlargement.

Primary pulmonary hypertension is a devastating disease of the heart and the lungs, manifest primarily by right heart failure. The only effective treatment of endstage primary pulmonary hypertension is transplantation of one or both lungs, or combined heart and lung transplantation. The current invention could be used as a treatment for the right heart failure and dilation of primary pulmonary hypertension.

Among the therapies for treatment of an enlarged heart, all strive to make the heart smaller. The purpose of the present invention is to make the ventricle small and/or to keep the ventricle small. The invention partitions the blood within the ventricle to protect the ventricle from the excessive volume and increased pressure of the blood.

BRIEF SUMMARY OF THE INVENTION

The invention described in this patent application is a device used to treat heart disease by decreasing the size of a diseased heart, or to prevent further enlargement of a diseased heart. The device works by limiting the volume of blood entering the heart during each cardiac cycle. The device is called a "diastolic volume limiting apparatus", or "divola" for short. The device partitions blood within the heart, and protects the heart from excessive volume and pressure of blood. This new invention is placed within the interior of the heart, particularly within the left ventricular cavity. The device is a hollow sac, with two openings, which simulates the shape and size of the interior lining of a normal heart. It allows the heart to fill through one opening juxtaposed to the annulus of the mitral valve to a predetermined, normal volume, and limits filling of the heart beyond that volume. It then allows blood to be easily ejected through the second opening through the aortic valve. By limiting the amount of blood entering the heart, the left ventricle is not subjected to the harmful effect of excessive volume and pressure of blood during diastole, the period of the cardiac cycle when the heart is at rest. This allows the heart to decrease in size, or to reverse remodel, and to recover lost function. In some applications, a second device, referred to as a "volume compensating device", or "VCD" for short, may be simultaneously placed inside the heart to take up excessive space between the heart and the primary device. This invention may be used to treat a variety of heart disease, most importantly diseases affecting the left ventricle. This invention is a significant improvement over mechanical heart assist devices because of its simplicity, durability, and significant cost benefit.

This invention may be used in patients who are denied heart transplantation because of the severe donor shortage. When configured for use in the right-ventricle, this invention may provide the only safe and effective treatment for primary pulmonary hypertension.

DETAILED DESCRIPTION OF THE INVENTION

The purpose of the invention is to allow for recovery of a diseased heart. The invention works by limiting the amount of blood that fills a ventricular cavity during each cardiac cycle. The primary device is called a diastolic volume limiting apparatus, or divola for short. The divola is a hollow plastic sac with two openings. The divola is usually placed within the left ventricular chamber of the heart. The divola is soft and compliant, and fills easily with blood to a certain, predetermined volume. When the divola has reached capacity, no further filling is allowed. By limiting filling of the left ventricle, the heart is not stretched by the excessive volume and pressure of blood. This allows for recovery of a diseased heart, or prevents progression or recurrence of heart disease. In some applications, a secondary device, called a volume compensating device or (VCD) may be simultaneously placed into the ventricle to take up excessive space between the ventricle and the primary device.

Figure 1:
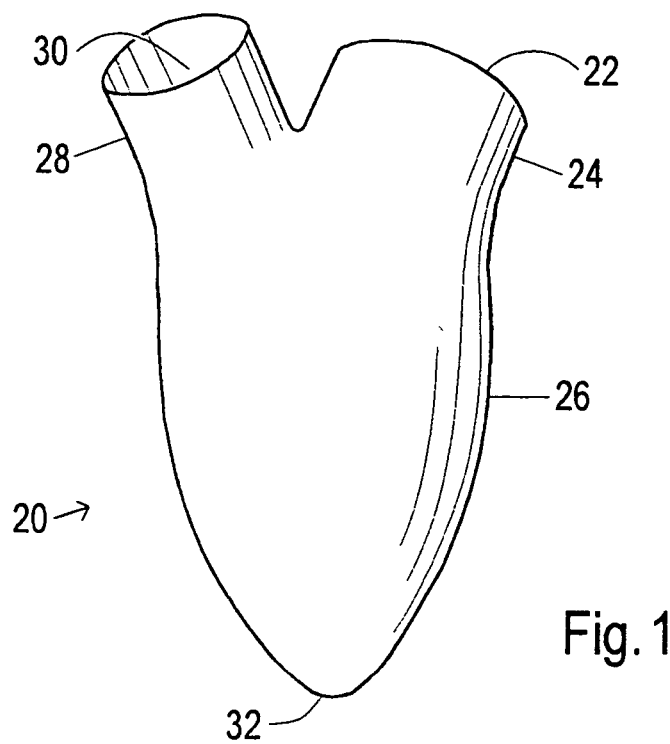
FIG. 1 is a frontal view of one embodiment of the diastolic volume limiting apparatus.
Figure 2:
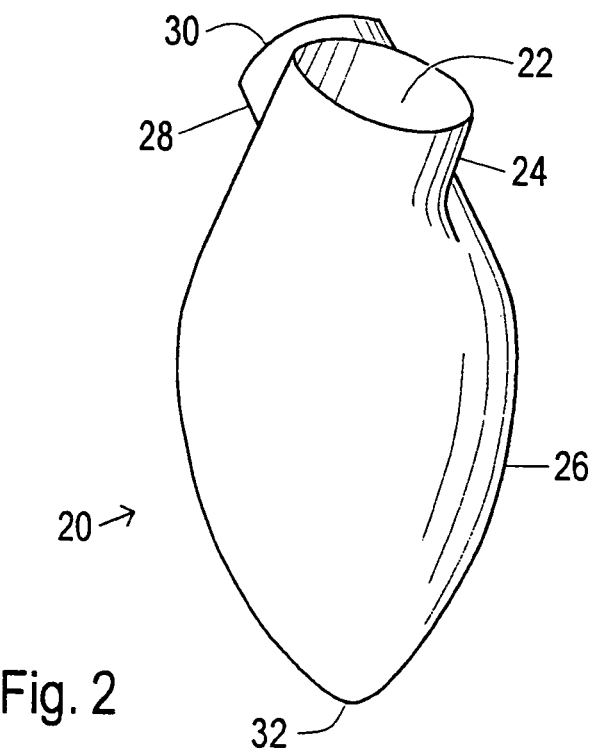
FIG. 2 is a left lateral view of one embodiment of the diastolic volume limiting apparatus.

The first component of the inventions, a diastolic volume limiting apparatus (divola) is shown in FIGS. 1 and 2. FIG. 1 depicts a divola 20 in a frontal view, and FIG. 2 depicts a divola 20 in a left side view. An inflow orifice 22 is an opening that allows blood to enter the divola. An inflow tract 24 is a hollow aspect of the device that directs blood from the inflow orifice 22 to a hollow body 26 of the divola. Blood is further directed from the body 26 of the divola through a hollow outflow tract 28 to an outflow orifice 30, where blood exits the divola. The body 26 of the divola tapers to an apex 32 of the divola. The shape and dimensions of the divola 20 mimic the shape and dimensions of the inner aspects of a healthy, non-dilated ventricle of a human heart. The inflow tract 24 and the outflow tract 28 are oriented in a three dimensional relationship to the body 26 of the divola in a manner similar to the orientation of the inflow valve and the outflow valve to a ventricle in an undiseased human heart. The body 26 and the apex 32 are flexible and pliable, but these areas of the divola do not easily stretch. The body 26 and apex 32 easily fill with blood to a predetermined volume or capacity, but they do not easily fill beyond that volume of capacity. The wall of the inflow tract 24 and the outflow tract 28 may be made thicker than the body 26 of the divola in order to provide more support for these areas. Both the inner aspect and the outer aspect of the inflow tract 24 and the outflow tract 28 may be roughened to allow ingrowth of tissue. The inflow tract 24 and the outflow tract 28 may be either cone-shaped or cylinder-shaped to accommodate a better fit with the corresponding valve annulus of the heart and with a prosthetic heart valve. The divola may be constructed of a single layer or multiple layers of biomedical material. The divola 20 may be made in several sizes to accommodate patients and hearts of different sizes.

The divola 20 illustrated in FIG. 1 and FIG. 2 is formed as a unitary seamless article from a flexible, resilient, blood compatible material. This material may be of any type suitable for pumping blood, such as certain types of polyurethanes. The material of which the sac is comprised should have long-term retention of physical strength under combined dynamic stressing and hydrolysis. The material should be of low toxicity and long-term stability for compatibility with blood. The material should also be of high strength, be capable of being repeatedly flexed, be capable of being sterilized, and be easily fabricated. Suitable materials are linear segmented polyurethanes, for example BIOMER from Ethicon. Other materials for manufacture include polytetrafluoroethylene, expanded polytetrafluroethylene, silicone rubber, and DACRON from DuPont, nitrile rubber, milar, and others.

One preferred method of making the divola comprises successively coating an accurately machined and polished aluminum mandrel whose outer surfaces define the inner surfaces of the sac. To form the sac, the coated mandrel is repeatedly dipped in the selected polymer solution and dried with rotation under infrared lamps. Additional dipping is done to thicken the inflow tract 24 and outflow tract 28. The dipping and drying steps are preferably performed under low humidity conditions. After dipping, the sac is annealed in a vacuum oven. The sac is washed thoroughly in distilled water, solvent extracted and dried in a vacuum oven. Alternately, a mold of breakable material, such as glass or porcelain may used to facilitate separation of the sac from the mold.

The second component of the invention is a volume compensating device (VCD). The VCD is used simultaneously with the divola in certain applications. The VCD is placed inside the heart with the divola. The VCD fits over the divola as a thimble fits over a finger. The VCD is a hollow, cone-shaped, balloon-like structure that may be selectively inflated or deflated to adjust the volume of the VCD. The VCD functions as a spacer to temporarily fill the void between the inner wall of the left ventricular chamber and the outer wall of the divola.

Figure 3:
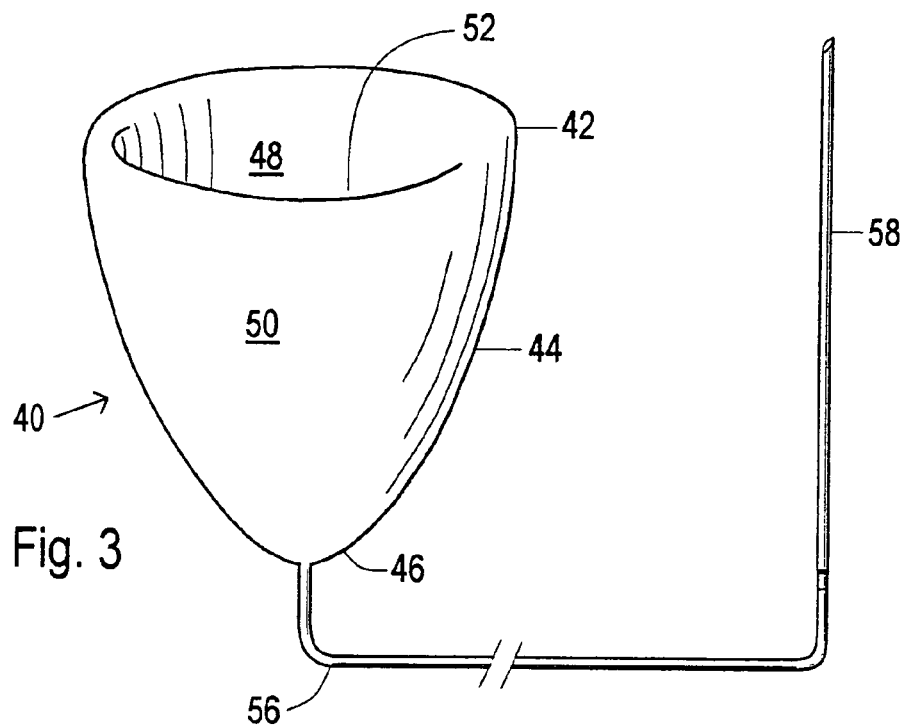
FIG. 3 is a perspective view of one embodiment of the volume-compensating device that has been deflated, with an attached trocar needle.

FIG. 3 is a perspective view of one embodiments of a VCD 40 that is deflated. The VCD 40 is a cone-shaped balloon that is divided into three regions; a base 42, a body 44, and an apex 46. The VCD has both an inner wall 48 and an outer wall 50. The inner wall 48 may be made thicker than the outer wall 50. A recess 52 is a concave and hollow aspect of the VCD defined by the inner wall 48. The shapes of the inner wall 48 and of the recess 52 are similar to the shape of the body 26 and the apex 32 of the divola. The dimensions of the recess 52 are slightly larger than the dimensions of the body 26 and apex 32 of the divola, in order for the VCD 40 to fit over the divola 20, as a thimble fits over a finger. An elongated access tube 56 connects to the apex 46 of the VCD 40, and communicates with the hollow interior of the VCD. The access tube 56 functions to allow inflation or deflation of the VCD 40. A trocar needle 58 is temporarily attached to the access tube 56 to facilitate passage of the access tube through tissues of the heart and the chest wall.

Figure 4:
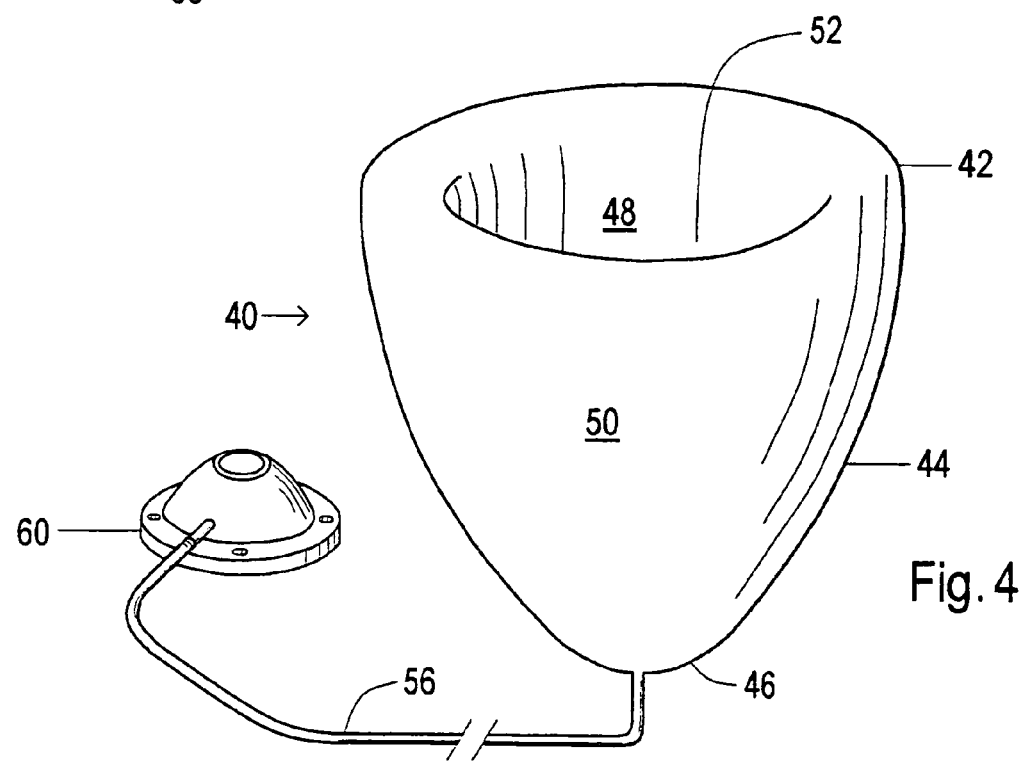
FIG. 4 is a perspective view of one embodiment of the volume-compensating device that has been partially inflated, with an attached access port.

FIG. 4 is a perspective view of one embodiment of a VCD 40 that is inflated. The VCD 40 has a base 42, a body 44, and an apex 46. During inflation, the inner wall 48 does not move or change shape. During inflation, the outer wall 50 moves away from the inner wall 48. During deflation, the outer wall 50 shrinks towards the inner wall 48, which does not move or change shape. The access tube 56 communicates with the hollow interior of the VCD 40 and allows for inflation and deflation. After implanted into the heart, the trocar needle 58 is detached and a commercially available access port 60, such as A-PORT from Arrow, is attached to the access tube. The access port 60 is then placed beneath the skin of the patient in a convenient location over the chest wall This allows for puncture of the access port 60 with a hypodermic needle that pierces the patient's skin to add or remove fluid, in order to inflate or deflate the VCD 40.

The volume-compensating device 40 illustrated in FIGS. 3 and 4 is formed as a unitary seamless article from flexible, resilient, blood compatible material. This material may be of any type suitable for contacting blood, such as certain types of siliconized rubber. The material of which the sac is comprised should have long-term retention of physical strength under combined dynamic stressing and hydrolysis. The material should be compliant to allow for easy inflation. The material should be of low toxicity and long-term stability for compatibility with blood. The material should also be of high strength, be capable of being repeatedly flexed, be capable of being sterilized and be easily fabricated. The volume-compensating device is ideally made of polyurethane. Other materials for manufacture include silicone rubber, polytetrafluroethylene, expanded polytetrafluroethylene, and nitrile rubber.

One preferred method of making the volume-compensating 40 device comprises successively coating an accurately machined and polished aluminum mandrel whose outer surfaces define the inner surfaces of the balloon. To form the balloon, the coated mandrel is repeatedly dipped in the selected polymer solution and dried with rotation under infrared lamps. The mandrel must be tipped to prevent trapping of air in the concave inner recess 52. Additional dipping is done to slightly thicken the apex 46. The inner wall 48 is thickened by pouring the selected polymer into the concave inner recess 52 for a brief time and then pouring the excess polymer out of the recess. The dipping and drying steps are preferably performed under low humidity conditions. After dipping, the sac is annealed in a vacuum oven. The sac is washed thoroughly in distilled water, solvent extracted and dried in a vacuum oven. The access tube 56 is then joined to the apex 46 of the volume compensating device with chemical or thermal bonding. Alternately, a mold of breakable material, such as glass or porcelain may used to facilitate separation of the sac from the mold.

Another method of manufacture of the volume compensating device is to mold the inner wall 48 and outer wall 50 separately, and join both either chemically or thermally near the base 42.

DESCRIPTION OF THE PREFERRED EMBODIMENT

A diastolic volume limiting apparatus (divola) has many applications in the treatment of heart disease. It may be placed in the heart at the time of a partial left ventriculectomy, the Batista operation, to prevent recurrent dilatation of the heart. A divola may also be placed in the heart after removal of a left ventricular assist device to prevent recurrent dilatation of the heart. Another use of the divola is for treatment of an ischemic ventricular septal defect to seal the leak between the left and the right ventricles. A divola may be placed to treat rupture of the left ventricular free wall secondary to acute myocardial infarction. A divola may be placed at the time of a mitral valve replacement to prevent further dilatation of the heart. A divola may be placed in the right ventricle to treat the right heart failure associated with primary pulmonary hypertension. The most common application of the divola is for treatment of dilated cardiomyopathy and other forms of chronic dilatation of the heart. A volume compensating device (VCD) would be used simultaneously in this use of the divola.

FIGS. 5, 6, 7, and 8 illustrate the major steps of surgical placement of a divola and a VCD. All four illustrations are frontal perspective views of the heart seen after opening the chest with a median sternotomy. A median sternotomy is a common incision made by sawing the breast bone down the middle.

Figure 5:
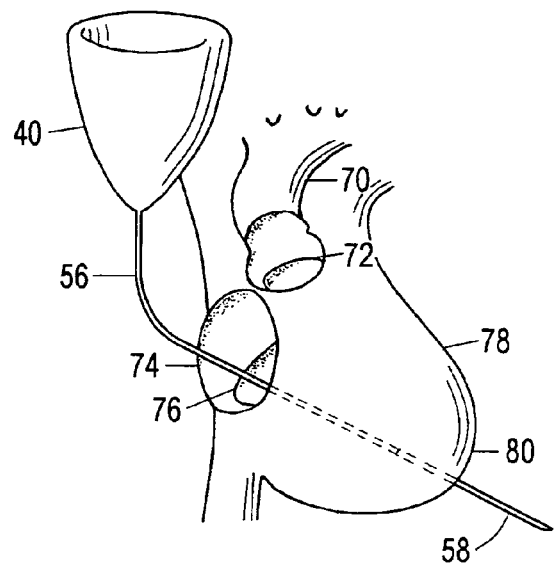
FIG. 5 is a perspective view showing the surgical placement of the volume-compensating device into the heart.

FIG. 5 shows details of placement of the VCD 40 into the heart. An incision is made in the aorta 70 to expose the native aortic valve 72. The leaflets of the aortic valve 72 are removed. Next, an incision is made into the left atrium 74 to expose the native mitral valve 76. The anterior leaflet of the mitral valve is removed. The VCD 40 is deflated. The trocar needle 58 of the divola 40 is passed through the mitral valve 76 and through the chamber of the left ventricle 78 and then punctures the apex 80 of the left ventricle. With gentle traction on the trocar 58 and on the access tube 56, the VCD 40 is drawn into the left ventricle 78.

Figure 6:
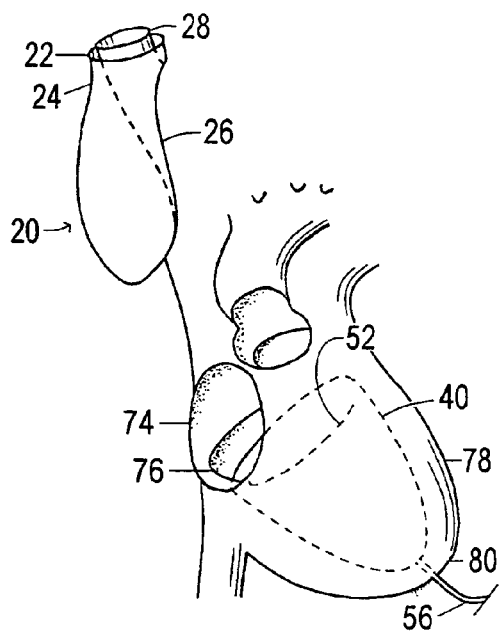
FIG. 6 is a perspective view showing the volume-compensating device in the left ventricle and the details of placement of the diastolic volume limiting apparatus into the heart.

FIG. 6 shows details of placement of the divola 20 into the left ventricle 78. The VCD 40 is shown within the left ventricle 78, with the access tube 56 emerging from the apex 80. The outflow tract 28 of the divola is invaginated into the body 26 and the inflow tract 24 of the divola and then brought out the inflow orifice 22. This maneuver makes the divola more compact for placement into the heart. The divola is then passed through the incision in the right atrium 74 and through the native mitral valve 76 into the recess 52 of the VCD, lying within the left ventricle 78.

Figure 7:
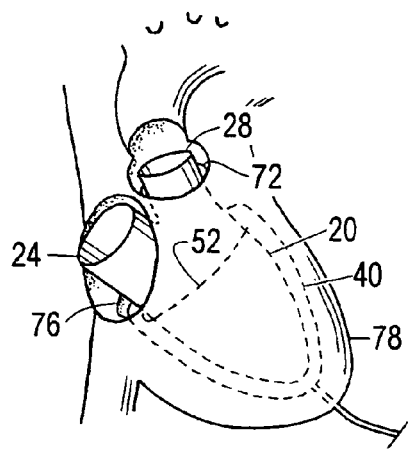
FIG. 7 is a perspective view showing the orientation of the diastolic volume limiting apparatus and the volume-compensating device within the left ventricular chamber of the heart.

FIG. 7 shows the placement of the divola 20 and the VCD 40 in the left ventricle 78. The divola 20 lies within the recess 52 of the VCD 40 as a finger fits into a thimble. The outflow tract 28 is exvaginated into its normal position. The divola 20 is rotated as needed to align the outflow tract 28 with the aortic valve 72 and to align the inflow tract 24 with the mitral valve 76.

Figure 8:
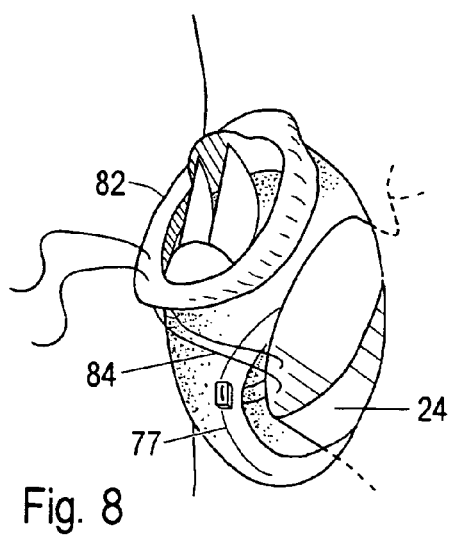
FIG. 8 is a perspective view of the details of sewing the diastolic volume limiting apparatus to a prosthetic mitral valve and to the mitral annulus of the heart.

FIG. 8 shows details of sewing a prosthetic mitral valve 82 and the inflow tract 24 to the mitral valve annulus 77. A commercially available prosthetic mitral valve prosthesis 82, such as MEDTRONIC HALL from Medtronic, of an appropriate size, is chosen. The inflow tract 24 is cut to appropriate length. Cardiac suture 84 is placed first in the mitral annulus 77, then the edge of the outflow tract 24, then the sewing ring of the prosthetic mitral valve 82. A complete series of similar sutures are placed around the circumference of the valve. The mitral valve prosthesis 82 and the inflow tract 24 are seated into the mitral valve annulus 77, and the cardiac sutures 84 are then tied and cut. The outflow tract and a prosthetic aortic valve such as MEDTRONIC HALL from Medtronic are similarly joined to the aortic valve annulus (not shown).

To complete the operation, the access tube 56 (FIG. 4) is connected to a commercially available infusion port 60 (FIG. 4) such as A-PORT from Arrow. The infusion port is placed in a convenient subcutaneous location such as the left anterior chest wall. The VCD is partially filled with sterile saline. Air is displaced from the chambers of the heart, and the incisions in the aorta 70 and in the left atrium 74 (FIG. 5) are closed with suture.

Figures 9, 10:
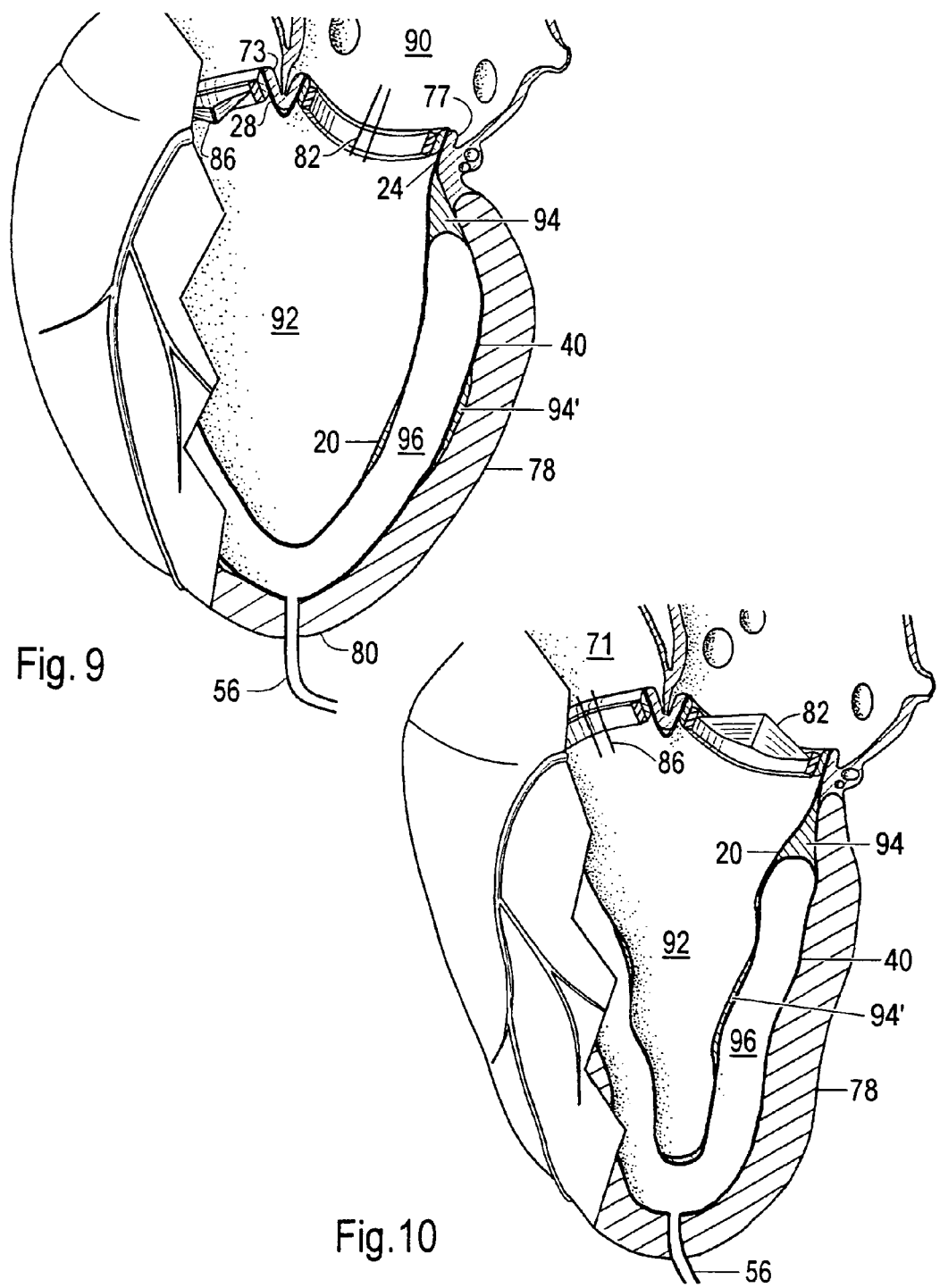
FIG. 9 is a partial cross section view of the diastolic volume limiting apparatus and the volume compensating device placed in the left ventricle of the heart, which is at rest, in diastole.
FIG. 10 is a partial cross section view similar to FIG. 9 but with the heart contracting, in systole.

FIG. 9 is a partial cross section anterior left-lateral view of a divola and a VCD placed in the left ventricle of a human heart. In FIG. 9 the heart is in diastole, the phase of the cardiac cycle when the heart is at rest. FIG. 10 is the same view as FIG. 9, but with the heart in systole, the phase of the cardiac cycle when the heart is contracting.

FIG. 9 shows the divola 20 within the interior of the left ventricle 78. The VCD 40 is also within the interior or the left ventricle 78, fitting over the divola 20 as a thimble would fit over a finger. A prosthetic mitral valve 82 has been placed in the inflow tract 24 of the divola. Both the prosthetic mitral valve 82 and the edged of the inflow tract 24 are sutured to the annulus of the mitral valve 77. A prosthetic aortic valve 86 has been placed in the outflow tract 28 of the divola. Both the prosthetic aortic valve 86 and the outflow tract 28 are sutured to the annulus of the aortic valve 73.

The access tube 56 penetrates the apex 80 of the left ventricle, and communicates with the interior space of the VCD, or intra-VCD space 96. The space between the interior surface of the left ventricle and the exterior surface of the divola is called the interstitial space 94, 94'. The VCD 40 lies within the interstitial space 94, 94', and functions to fill the void within this space. The VCD 40 may be variable inflated or deflated to adjust the volume of the VCD (and consequently the volume of the interstitial space 94, 94'). As depicted in FIGS. 9 and 10, the VCD 40 has been partially inflated with saline solution. The space within the divola is referred to as the intradivolar space 92.

During diastole, blood from the left atrial chamber 90 crosses the open mitral valve prosthesis 82 to fill the intradivolar space 92. The divola 20 acts as a partition or to separate the intradivolar space 92 from the interstitial space 94, 94'. In heart disease, the left atrial pressure is elevated, as well as the pressure in the left ventricle. When a divola 20 is placed in the left ventricle 78, the pressures within the interstitial space 94, 94' are low during diastole, protecting the left ventricle 78 from the harmful effect of these high pressures.

Restated, the divola 20 functions to segregate and to partition blood from contacting the interior the left ventricle 78. The divola has a limited capacity, and will not fill with blood beyond that capacity. The capacity of the diseased left ventricle 78 is greater than the capacity of the divola 20, and therefore, the pressure within the interior of the left ventricle 78 is low, despite high pressures within the intradivolar space 92. The divola dose not actively pump blood, but relies on the power of the left ventricle to pump blood.

FIG. 10 depicts a divola 20 and a VCD 40 implanted into the left ventricle 78 of a heart during systole, the period of the cardiac cycle when the heart contracts. The left ventricular contraction causes a rapid increase of pressure the interstitial space 94, 94', the intra-VCD space 96, and in the intra-divolar space 92. This high pressure within the divola causes the mitral valve prosthesis 82 to close and the prosthetic aortic valve 86 open. The ventricular contraction forces blood out of the divola 20 through the aortic valve prosthesis 86 into lumen of the aorta 71. Because the VCD 40 lies within the interstitial space 94, 94' the pressure within the VCD, or intra-VCD space 96 is equal to the pressure in the interstitial space 94, 94'. This pressure is conducted through the interior of the access tube 56 and interior of the access port 60 (FIG. 4). A needle may be placed through the skin of a patient into the access port to measure and record the interstitial space pressure. A needle placed in the access port 60 allows for fluid to be added or removed from the VCD 40.

FIGS. 11 thru 14 are plots of the pressures within the various spaces of the heart, divola, and VCD in various situations.

Figure 11:
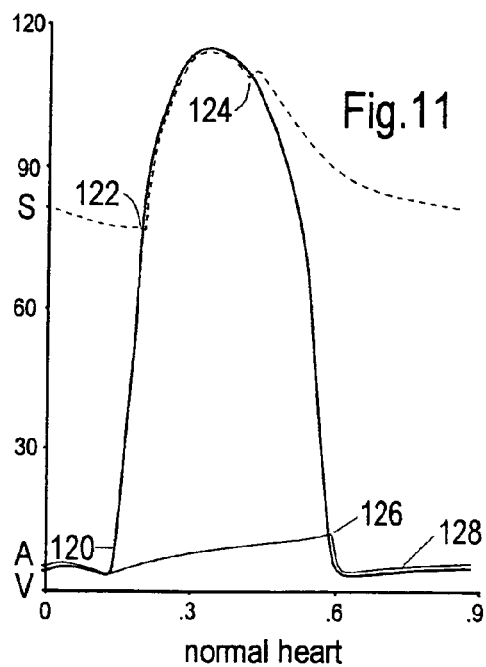
FIG. 11 is a plot showing the pressures within a normal heart.

FIG. 11 shows the pressure within the chambers of a normal heart. The horizontal axis shows time in seconds and the vertical axis shows pressure in millimeters mercury. The systemic arterial pressure or blood pressure (S) is indicated by a dashed fine line adjacent to the vertical axis. The left ventricular pressure (V) is indicated by a solid bold line. The left atrial pressure (A) is indicated by a solid fine line. Systole is defined as the phase of the cardiac cycle when the heart contracts and ejects blood. Systole begins at event 120 with a rapid rise in the left ventricular pressure. Simultaneously, the mitral valve closes. At event 122 the pressure in the left ventricle exceeds the aortic pressure, resulting in opening of the aortic valve and ejection of the blood from the left ventricle into the aorta. At event 124 the left ventricular pressure falls below the aortic pressure, resulting in closure of the aortic valve. This event marks the end of systole and the beginning of diastole. Diastole is defined as the phase of the cardiac cycle when the heart is relaxed and fills with blood. When the left ventricular pressure falls below the left atrial pressure, event 126, the mitral valve opens, resulting in flow of blood from the left atrium to fill the left ventricle. During the middle of diastole, event 128, the left ventricular pressure and the left atrial pressures are essentially equal. In the undiseased state, the left atrial pressure and the left ventricular diastolic pressure are both low.

Figure 12:
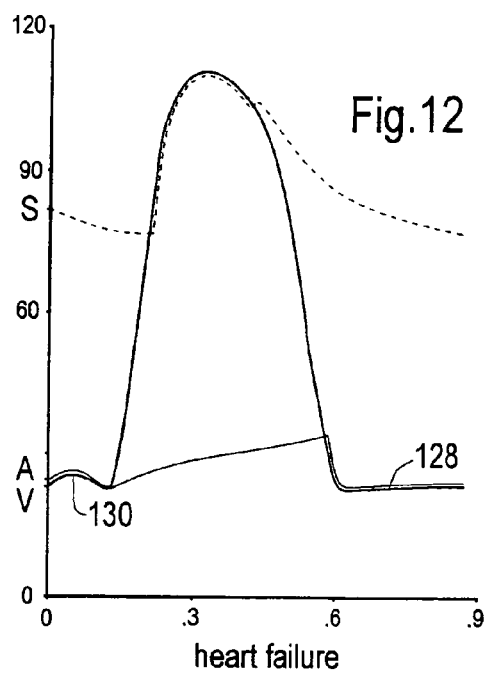
FIG. 12 is a plot showing the pressures within a heart with heart failure.

FIG. 12 shows the intracardiac pressures as in FIG. 11 but in a patient with heart failure, before implantation of a divola and a VCD. During mid diastole 128 and late diastole 130, both the left atrial pressure (A) and the left ventricular pressure (V) are elevated. The two pressures are essentially equal during diastole because the two chambers are in communication through an open mitral valve. The elevated left ventricular pressure may cause persistent and worsening enlargement of the left ventricular cavity. Despite conventional medical or surgical therapies, reverse remodeling of the diseased heart may be prevented because of the persistent elevation of left atrial and left ventricular pressure.

Figure 13:
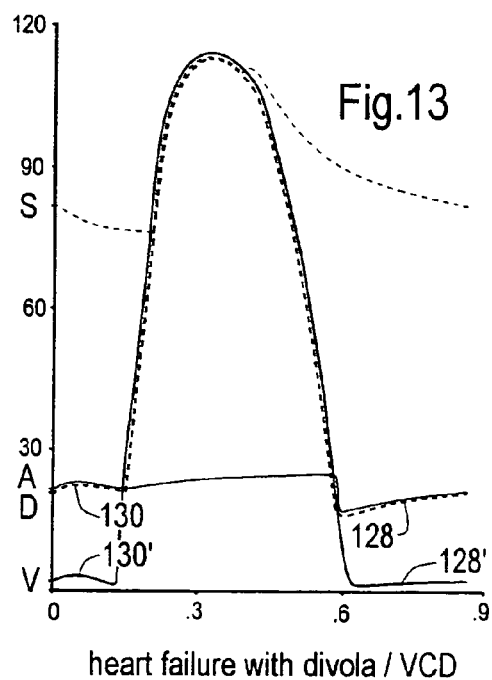
FIG. 13 is a plot showing the pressures within a heart with heart failure, after placement of a diastolic volume limiting apparatus and a volume-compensating device.

FIG. 13 shows the pressure within the chambers of the heart in a patient with heart failure after implantation of a divola and a VCD. As in FIGS. 11 and 12, the systemic arterial pressure (S) is drawn as a dashed fine line and the left atrial pressure (A) as a solid fine line. When a divola and a VCD are implanted, the left ventricular pressure, the pressure within the interstitial space 94 (FIGS. 9 and 10), and the pressure within the intra-VCD space 96 (FIGS. 9 and 10), are all equal. This left ventricular pressure (V) is depicted as a solid black line. The pressure within the divola, or intradivolar pressure (D) is drawn as a dashed bold line.

The left atrial pressure is elevated during both systole and diastole. During mid diastole 128 and late diastole 130 the intradivolar pressure is elevated. This is because the intradivolar space is in communication with the high pressure in the left atrium through an open mitral valve. However, because the divola segregates blood within the left ventricle, the pressure within the left ventricle during diastole 128', 130', is very low, essentially zero. The segregation of the volume and pressure of blood within the heart by the divola protects the left ventricle from the harmful effect of elevated pressure during diastole.

Figure 14:
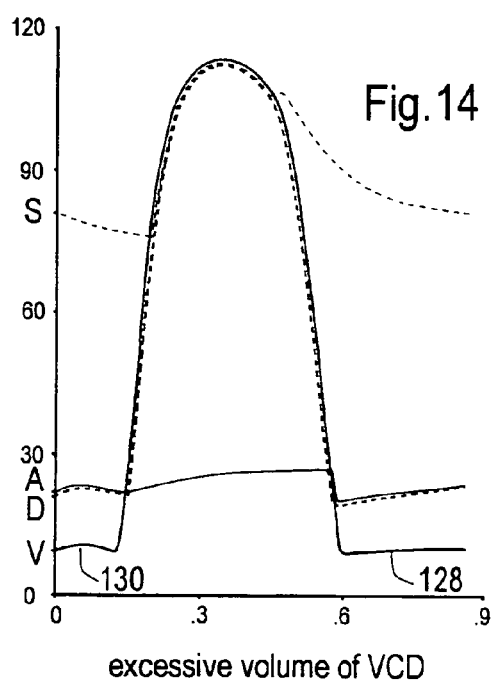
FIG. 14 is a plot showing the pressures within a heart with heart failure with excessive volume in the implanted volume-compensating device.

FIG. 14 shows the pressure within the chambers of the heart in a patient with heart failure at an interval of time after implantation of a divola and a VCD. During this interval, the left ventricle has reverse remodeled or decreased in size to some degree. Consequently, the capacity of the left ventricle is decreased, and the left ventricular pressure rises, as shown in late diastole 130 and mid diastole 128. The left ventricular pressure, or interstial space pressure, may be recorded by placing a needle in the access port 54 (FIG. 4). With removal of some of the volume of fluid within the VCD through the access port, the intraventricular pressure immediately falls to near zero, as shown 128', 130' in FIG. 13.

In the weeks and months following implantation of the divola and VCD, the enlarged left ventricle continues to reverse remodel or shrink to a more normal size. This requires interval removal of fluid from the VCD. The intraventricular pressure is measured by placing a needle in the access port and recording the pressure. If the intraventricular pressure (intra VCD pressure) is elevated, there has been further shrinking of the left ventricle, and more fluid should be removed from the VCD.

Figure 15:
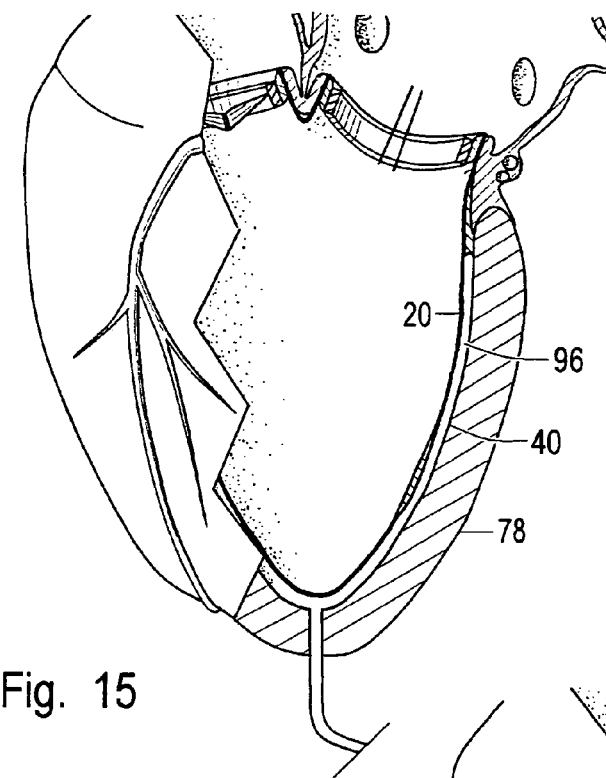
FIG. 15 is a partial cross section view of a diastolic volume limiting apparatus and a deflated volume-compensating device in the left ventricle of a heart that has reverse remodeled, during diastole.
Figure 16:
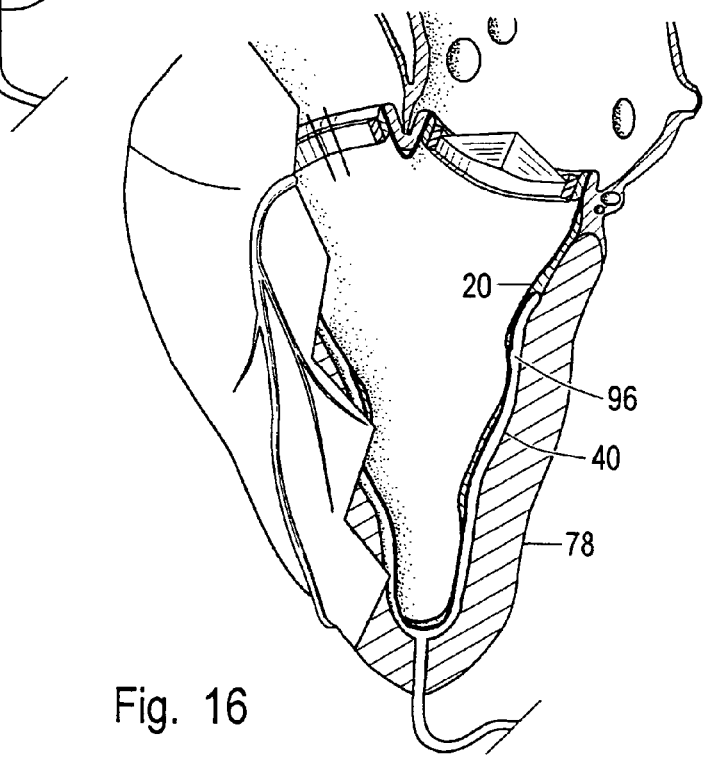
FIG. 16 is a partial cross section view similar to FIG. 15, but with the heart contracting, in systole.

The heart potentially can shrink to a size such that the space filling effect of the VCD is not needed at all, and all of the volume of fluid within the VCD may be permanently removed. FIG. 15 depicts a heart during diastole in which the left ventricle 78 has shrunken or reverse remodeled. FIG. 16 depicts the same situation in a heart but during systole. In both FIGS. 15 and 16, the VCD 40 has been deflated, and the volume of the intra-VCD 96 space is small. The left ventricle 78 has shrunken around the divola 20, and has regained a shape similar to a normal, healthy heart.

I claim:

1. A method of treating a diseased heart including the steps of:
   a. creating a hollow plastic sac with two openings, said sac being soft and compliant so that it will fill easily with blood to a certain, predetermined volume, but when the sac has reached capacity, no further expansion is allowed;
   b. creating a volume compensating device shaped to surround a significant portion of said sac, said volume compensating device having a hollow interior enabling the device to expand and contract upon the increase or decrease of fluid inside said hollow interior;
   c. creating an access tube joined to said volume compensating device in continuity with said hollow interior;
   d. inserting said device in the ventricle of the heart;
   e. inserting the said sac inside said device;
   f. connecting one of said openings in said sac to the annulus of the inflow valve of the ventricle;
   g. connecting the other of said openings in said sac to the annulus of the outflow valve of the ventricle;
   h. placing a fluid inside said hollow interior; and
   i. periodically removing fluid from said hollow interior in an incremental, stepwise, manner to permanently decrease the size of said device.

2. The method of claim 1 including the additional steps of forming the sac so that when the sac is filled to capacity, it will appear generally in size and shape to match the size and shape of a ventricle of an undiseased human heart.

3. In combination, a sac for insertion in a chamber of a heart, said sac having a predetermined capacity which limits the amount of blood that can be received in said sac, and a volume compensation device shaped to fit about at least a portion of said sac, said device sized and shaped to substantially fill the area between the sac, when filled to capacity, and the wall of a chamber of the heart when the sac and device are inserted inside the chamber.

4. The combination of claim 3 further including an expansion chamber in said device for receiving a fluid and a tube connected to said expansion chamber for retracting a portion of the fluid in said expansion chamber to reduce the size of the device.

5. In combination, a device for insertion into the ventricular cavity of a heart, consisting of
   a. an inner hollow plastic sac, with two openings, for limiting filling of the ventricle, and b. an outer sac, surrounding said inner sac, creating a space between the inner sac and the ventricular cavity with variable volume, to compensate for variable volume of said ventricular cavity;

c. an access tube connected to said space and communicating with a subcutaneous access port.

6. The combination of claim 5 further including and inflow tract to allow entry of blood into the device, and an outflow tract to allow exit of blood from the device.

7. The apparatus of claim 5 further including an access tube having opposing ends, one end communicating with said space and the other end communicating with an access port.

8. The combination of claim 6 having an inflow valve incorporated into the inflow tract.

9. The combination of claim 6 having an outflow valve incorporated into the outflow tract.

10. The combination of claim 6 having both an inflow valve incorporated into the inflow tract and an outflow valve incorporated into the outflow tract.

11. The combination of claim 6 constructed so that it may be placed into the ventricular cavity of a heart in a minimally invasive manner.

12. The combination of claim 6 having an inflow valve incorporated into the inflow tract, constructed so that said device may be placed into the ventricular cavity of a heart in a minimally invasive manner.

13. The combination of claim 6 having an outflow valve incorporated into the outflow tract, constructed so that said device may be placed into the ventricular cavity of a heart in a minimally invasive manner.

14. The combination of claim 6 having both an inflow valve and an outflow valve incorporated into the inflow tract and said outflow tract, constructed so that said device may be placed into the ventricular cavity of a heart in a minimally invasive manner.

* * * * *